(12) United States Patent
Cameron et al.

(10) Patent No.: US 8,168,811 B2
(45) Date of Patent: May 1, 2012

(54) PRECURSORS FOR CVD/ALD OF METAL-CONTAINING FILMS

(75) Inventors: Thomas M. Cameron, Newtown, CT (US); Chongying Xu, New Milford, CT (US); Tianniu Chen, Rocky Hill, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 378 days.

(21) Appl. No.: 12/507,048

(22) Filed: Jul. 21, 2009

(65) Prior Publication Data

US 2010/0018439 A1  Jan. 28, 2010

Related U.S. Application Data

(60) Provisional application No. 61/082,824, filed on Jul. 22, 2008.

(51) Int. Cl.
*C07F 9/00* (2006.01)
*C07F 15/00* (2006.01)
*C07F 5/06* (2006.01)

(52) U.S. Cl. ........ 556/42; 556/45; 556/56; 556/57; 556/89; 556/116; 556/130; 556/137; 556/146; 556/182; 556/410; 106/287.19; 106/287.25

(58) Field of Classification Search ............ 106/287.19, 106/287.25; 556/54, 42, 45, 56, 57, 89, 116, 556/130, 137, 146, 182, 410
See application file for complete search history.

(56) References Cited

U.S. PATENT DOCUMENTS

| | | | |
|---|---|---|---|
| 5,453,494 A | 9/1995 | Kirlin et al. |
| 5,820,664 A | 10/1998 | Gardiner et al. |
| 5,840,897 A | 11/1998 | Kirlin et al. |
| 5,916,359 A | 6/1999 | Baum et al. |
| 5,919,522 A | 7/1999 | Baum et al. |
| 6,110,529 A | 8/2000 | Gardiner et al. |
| 6,126,996 A | 10/2000 | Kirlin et al. |
| 6,214,105 B1 | 4/2001 | Hintermaier et al. |
| 6,218,518 B1 | 4/2001 | Baum et al. |
| 6,277,436 B1 | 8/2001 | Stauf et al. |
| 6,284,654 B1 | 9/2001 | Roeder et al. |
| 6,340,769 B1 | 1/2002 | Baum et al. |
| 6,344,079 B1 | 2/2002 | Baum |
| 6,444,264 B2 | 9/2002 | Hintermaier et al. |
| 6,599,447 B2 | 7/2003 | Stauf et al. |
| 7,226,640 B2 | 6/2007 | Baum et al. |
| 7,323,581 B1 | 1/2008 | Gardiner et al. |
| 2006/0035462 A1 | 2/2006 | Millward |
| 2007/0134417 A1 | 6/2007 | Baum et al. |
| 2008/0254218 A1 | 10/2008 | Lei et al. |
| 2009/0112009 A1 | 4/2009 | Chen et al. |
| 2009/0208637 A1 | 8/2009 | Chen et al. |
| 2009/0321733 A1 | 12/2009 | Gatineau et al. |

FOREIGN PATENT DOCUMENTS

| | | |
|---|---|---|
| WO | 2004046417 A2 | 6/2004 |
| WO | 2006012052 A2 | 2/2006 |
| WO | 2008057616 A2 | 5/2008 |
| WO | 2008128141 A2 | 10/2008 |
| WO | 2009059237 A2 | 5/2009 |

OTHER PUBLICATIONS

Belot et al., Chemical Vapor Deposition, vol. 5, No. 5, pp. 65-69 (1999).*
Karsch, H. et al., "Bis(amidinate) Complexes of Silicon and Germanium", "Eur. J. Inorg. Chemistry", 1998, pp. 433-436.
Unpublished U.S. Appl. No. 12/434,485, filed May 1, 2009.
Unpublished U.S. Appl. No. 12/392,009, filed Feb. 24, 2009.
Unpublished U.S. Appl. No. 12/523,704, filed Jul. 17, 2009.

* cited by examiner

*Primary Examiner* — Porfirio Nazario Gonzalez
(74) *Attorney, Agent, or Firm* — Hultquist, PLLC; Steven J. Hultquist; Maggie Chappuis

(57) ABSTRACT

Precursors useful for vapor phase deposition processes, e.g., CVD/ALD, to form metal-containing films on substrates. The precursors include, in one class, a central metal atom M to which is coordinated at least one ligand of formula (I):

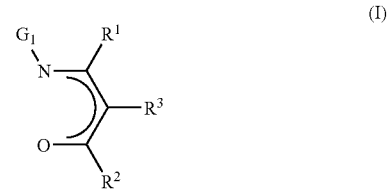

(I)

wherein:
$R^1$, $R^2$ and $R^3$ are each independently H or ogano moieties; and
$G_1$ is an electron donor arm substituent that increases the coordination of the ligand to the central metal atom M;
wherein when $G_1$ is aminoalkyl, the substituents on the amino nitrogen are not alkyl, fluoroalkyl, cycloaliphatic, or aryl, and are not connected to form a ring structure containing carbon, oxygen or nitrogen atoms. Also disclosed are ketoester, malonate and other precursors adapted for forming metal-containing films on substrates, suitable for use in the manufacture of microelectronic device products such as semiconductor devices and flat panel displays.

19 Claims, 1 Drawing Sheet

PRECURSORS FOR CVD/ALD OF METAL-CONTAINING FILMS

CROSS REFERENCE TO RELATED APPLICATION

This application claims the benefit of priority under 35 USC §119 of U.S. Provisional Patent Application No. 61/082,824 filed Jul. 22, 2008. The disclosure of U.S. Provisional Patent Application No. 61/082,824 is hereby incorporated herein by reference in its entirety, for all purposes.

FIELD OF THE INVENTION

The present invention relates to precursors useful for depositing metal-containing films on substrates, e.g., precursors useful for forming high dielectric constant films for the manufacture of microelectronic devices, such as dynamic random access memory (DRAM) devices. More specifically, the invention relates in one aspect to strontium and barium ketoiminate complexes useful for such purpose, having applicability to atomic layer deposition or other vapor deposition processes, e.g., for forming films such as strontium titanate and barium strontium titanate.

DESCRIPTION OF THE RELATED ART

In the manufacture microelectronic devices, a wide variety of precursors are employed for deposition of films containing metals, e.g., Group II metals, such as strontium titanate (STO) and barium strontium titanate (BST) films. These precursors include organometallic barium and strontium compounds and complexes that are utilized to form high dielectric constant (high k) films on microelectronic substrates, by film-forming techniques such as chemical vapor deposition (CVD) and atomic layer deposition (ALD).

Deposition of conformal Ba— or Sr-containing high k materials using CVD/ALD techniques requires metal precursors that are transportable (volatile) and thermally stable at temperatures specific to the ALD processes that are employed. Volatile monomeric barium and strontium precursors are therefore desired for such applications. Unfortunately, however, both Sr and Ba tend to form polymeric or oligomeric complexes that are either in-volatile or non-volatile.

The art continues to seek improved precursors having utility for vapor phase deposition processes, including strontium and barium precursors having suitable volatilization and thermal stability characteristics, and resistance to oligomerization or polymerization.

More generally, the art seeks improved precursors for vapor deposition of a wide variety of metals for the manufacture of microelectronic devices products

SUMMARY OF THE INVENTION

The present invention relates to precursors useful for vapor phase deposition processes, to form metal-containing films on substrates.

The invention relates in one aspect to a precursor including a central metal atom M to which is coordinated at least one ligand of formula (I):

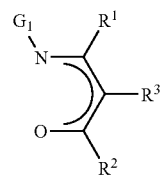

wherein:
$R^1$, $R^2$ and $R^3$ are each independently H or ogano moieties; and
$G_1$ is an electron donor arm substituent that increases the coordination of the ligand to the central metal atom M;
wherein when $G_1$ is aminoalkyl, the substituents on the amino nitrogen are not alkyl, fluoroalkyl, cycloaliphatic, or aryl, and are not connected to form a ring structure containing carbon, oxygen or nitrogen atoms.

In another aspect, the invention relates to a ketoiminate precursor including a central metal atom selected from Ba and Sr, to which is coordinated multiple ketoiminate ligands, wherein the ketoiminate ligands are coordinated at their nitrogen and oxygen atoms to the central strontium or barium atom, with the nitrogen having a pendant side arm substituent thereon including a neutral donor group capable of interacting with the strontium or barium central atom, and the α-carbons each being substituted with an organo substituent.

A further aspect of the invention relates to a precursor of the formula

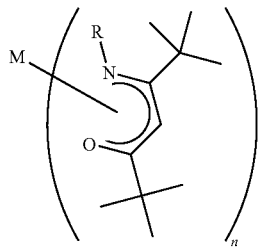

wherein R is a functional group including pendant side arm functionality that provides electron donor character, n is the valence of the metal M, and M is selected from the group consisting of Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr and Ru.

In a further aspect, the invention relates to a precursor of the formula

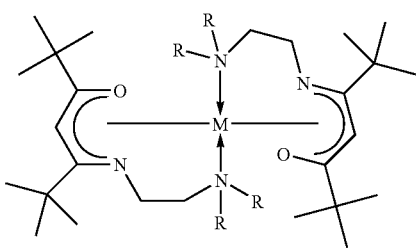

wherein both Rs on the nitrogen atom are not simultaneously alkyl.

Another aspect of the invention relates to a precursor complex that may be of the formula

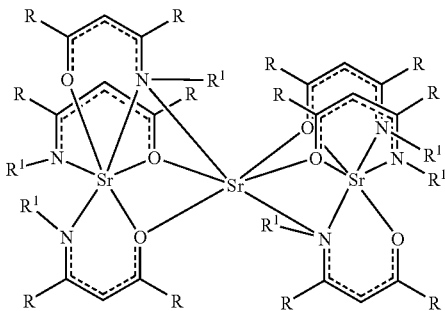

wherein each of the α-carbon R groups is independently selected from among alkyl, fluoroalkyl, clycloaliphatic and aryl, having from one to 10 carbon atoms, and each of the $R^1$ substituents is a stabilization donor side arm group independently selected from among alkoxyalkyloxyalkyl, hydrazidyl, aminoalkylaminoalkyl, alkoxyphenyl, alkoxyphenylalkyl, aminoalkyl, and aminophenyl, wherein: the alkyl and alkoxy groups contain 1-3 carbon atoms; amino is —$NH_2$ or monoalkylamino wherein the alkyl on the amino contains 1-3 carbon atoms; and wherein the alkoxyphenyl may optionally be additionally substituted on the phenyl ring by up to two alkyl and/or alkoxy groups, each containing 1-3 carbon atoms.

In a further aspect, the invention relates to a precursor including a metal M to which is coordinated a ligand selected from among

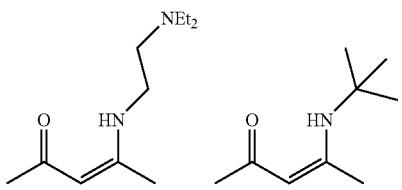

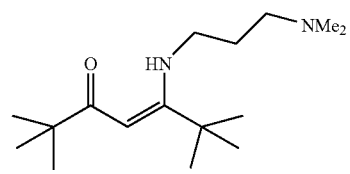

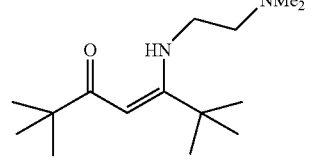

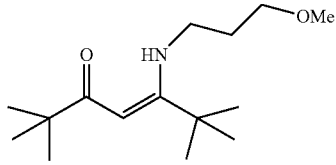

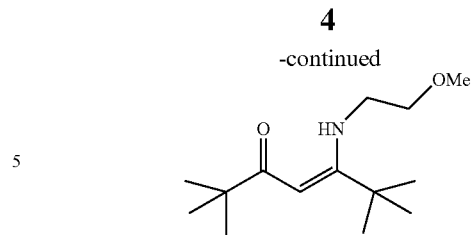

Another aspect of the invention relates to a strontium precursor, selected from among the following strontium compounds

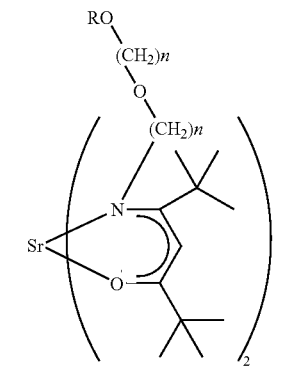

n = 1, 2, 3

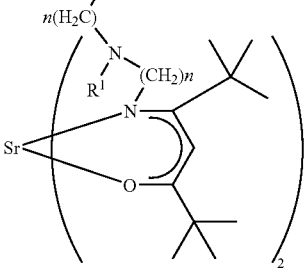

n = 1, 2, 3

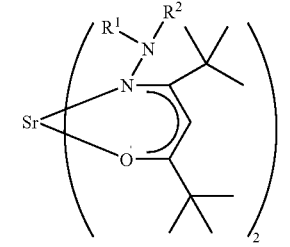

wherein R, $R^1$, $R^2$, and $R^3$, as applicable, are independently selected from among H, $C_1$-$C_8$ alkyl, $C_1$-$C_8$ alkoxy, $C_3$-$C_{10}$ cycloaliphatic and $C_6$-$C_{12}$ aryl.

A still further aspect of the invention relates to a precursor comprising at least one ligand selected from among beta-enaminoester and beta-iminoestrate ligands coordinated to a metal central atom of a metal selected from among main group metal elements, lanthanides, and transition metals.

Yet another aspect of the invention relates to a precursor selected from among (I) and (II):

(I) ketoesters of the formula $(R)_nM[(R^1O)C(=O)C(R^2)C(O)(R^3)]_{OX-n}$, wherein each of R, $R^1$, $R^2$ and $R^3$ is independently selected from among H, $C_1$-$C_8$ alkyl, $C_1$-$C_8$ alkoxy, $C_3$-$C_{10}$ cycloaliphatic and $C_6$-$C_{12}$ aryl, and R can additionally be —O(CR⁴R⁵)ₘO—, wherein each of R⁴ and R⁵ is independently selected from among H, $C_1$-$C_8$ alkyl, $C_1$-$C_8$ alkoxy, $C_3$-$C_{10}$ cycloaliphatic and $C_6$-$C_{12}$ aryl and m is an integer having a value of from 1 to 3, OX is the oxidation state of the metal M, and m is an integer having a value of from 0 to OX; and malonates of the formula $(R)_nM[(R^1O)C(=O)C(R^2)C(O)(OR^3)]_{OX-n}$, wherein each of R, $R^1$, $R^2$ and $R^3$ is independently selected from among H, $C_1$-$C_8$ alkyl, $C_1$-$C_8$ alkoxy, $C_3$-$C_{10}$ cycloaliphatic and $C_6$-$C_{12}$ aryl, and R can additionally be —O(CR⁴R⁵)ₘO—, wherein each of R⁴ and R⁵ is independently selected from among H, $C_1$-$C_8$ alkyl, $C_1$-$C_8$ alkoxy, $C_3$-$C_{10}$ cycloaliphatic and $C_6$-$C_{12}$ aryl and m is an integer having a value of from 1 to 3, OX is the oxidation state of the metal M, and n is an integer having a value of from 0 to OX.

A further aspect of the invention relates to a precursor composition comprising a precursor as variously described above, in a solvent medium.

Another aspect relates to a precursor source package comprising a precursor storage and dispensing vessel holding a precursor as variously described above.

In a further aspect, the invention relates to a method of forming a metal-containing film on a substrate, comprising volatilizing a precursor as variously described above, to form a precursor vapor, and contacting the precursor vapor with the substrate to deposit said film on the substrate.

Another aspect of the invention relates to a method of manufacturing a microelectronic product, comprising use of a precursor or precursor composition as variously described above.

A still further aspect of the invention relates to a titanium precursor selected from among:

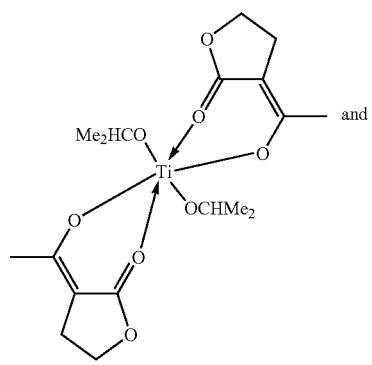

and

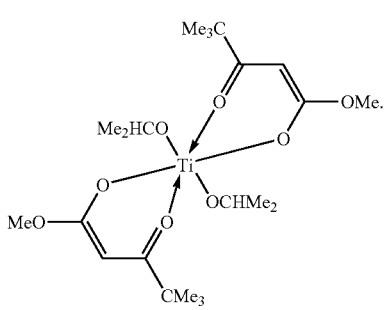

Another aspect of the invention relates to a method of making a titanium precursor of claim 37, comprising conducting a corresponding one of the following reactions:

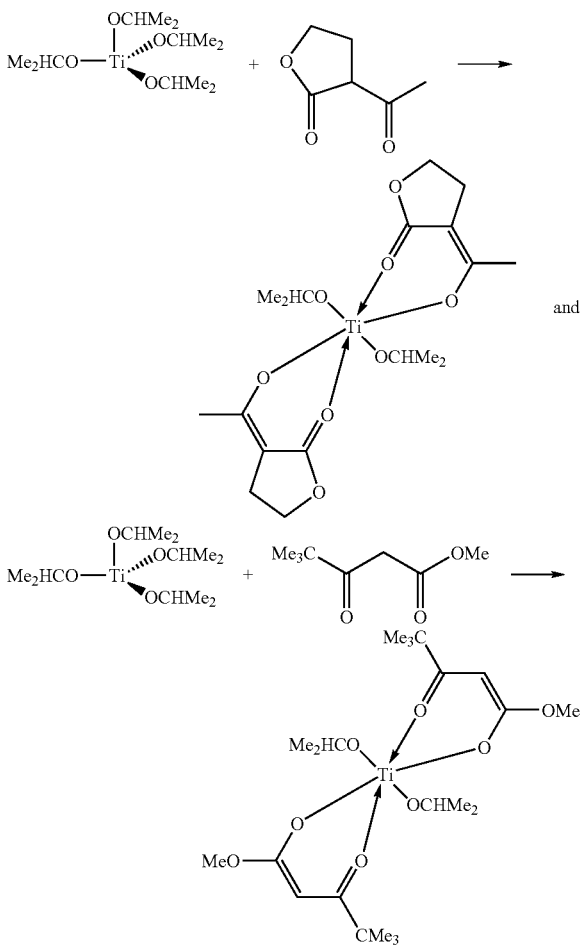

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
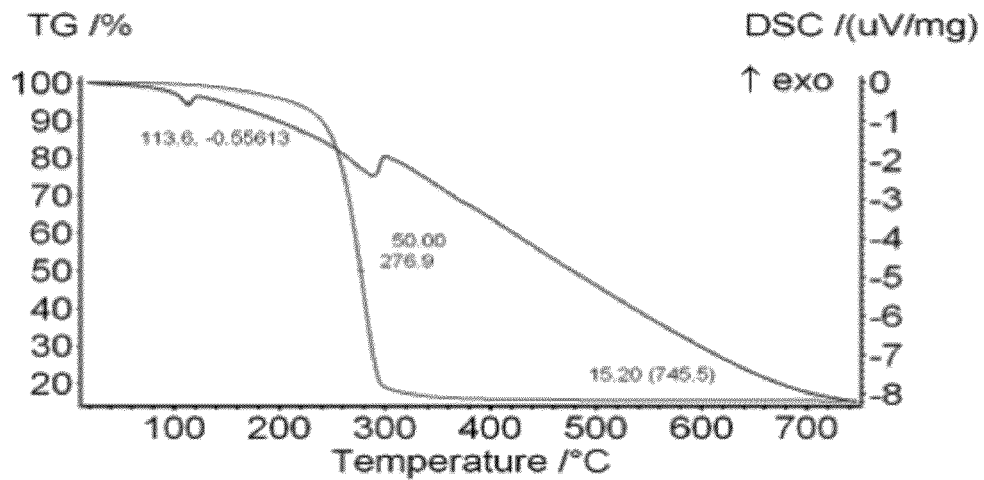
FIG. 1 is an STA plot for a strontium ketoiminate complex, having α-carbon t-butyl substituents, and a diethylaminoethyl donor arm stabilization group on the ketoiminate N atom.

The present invention relates to metal precursors having utility for forming metal-containing films on substrates, e.g., in the manufacture of microelectronic devices and device structures.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer.

As used herein, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range.

The precursors of the invention may be further specified in specific embodiments by provisos or limitations excluding specific substituents, groups, moieties or structures, in relation to various specifications and exemplifications thereof set forth herein. Thus, the invention contemplates restrictively defined compositions, e.g., a composition wherein $R^i$ is $C_1$-$C_{12}$ alkyl, with the proviso that $R^i \neq C_4$ alkyl when $R^j$ is silyl.

"Alkyls" as used herein include, but are not limited to, methyl, ethyl, propyl, isopropyl, butyl, s-butyl, t-butyl, pentyl and isopentyl and the like. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. "Cycloalkyls" as used herein include, but are not limited to cyclopropyl, cyclobutyl, cyclopentyl, cyclohexyl and the like. In all chemical formulae herein, a range of carbon numbers will be regarded as specifying a sequence of consecutive alternative carbon-containing moieties, including all moieties containing numbers of carbon atoms intermediate the endpoint values of carbon number in the specific range as well as moieties containing numbers of carbon atoms equal to an endpoint value of the specific range, e.g., $C_1$-$C_6$, is inclusive of $C_1$, $C_2$, $C_3$, $C_4$, $C_5$ and $C_6$, and each of such broader ranges may be further limitingly specified with reference to carbon numbers within such ranges, as sub-ranges thereof. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

The invention, as variously described herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the invention.

The present invention relates in one aspect to precursors having a central metal atom M to which is coordinated at least one ligand of formula (I):

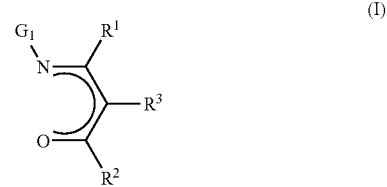

wherein:
$R^1$, $R^2$ and $R^3$ are each independently H or ogano moieties; and
$G_1$ is an electron donor arm substituent that increases the coordination of the ligand to the central metal atom M;
wherein when $G_1$ is aminoalkyl, the substituents on the amino nitrogen are not alkyl, fluoroalkyl, cycloaliphatic, or aryl, and are not connected to form a ring structure containing carbon, oxygen or nitrogen atoms.

The metal in the foregoing formula may be of any suitable type to which at least one ligand of the above-discussed formula is coordinatable, e.g., Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr and Ru.

The metal species in certain specific embodiments is selected from among calcium, strontium, barium, scandium, yttrium, lanthanum, titanium, zirconium, vanadium, tungsten, manganese, cobalt, iron, nickel, ruthenium, zinc, copper, palladium, platinum, iridium, rhenium, and osmium.

In various embodiments of the metal precursors of the above formula, $R^1$ and $R^2$ can be the same as or different from one another, with each being independently selected from among alkyl, fluoroalkyl, cycloaliphatic and aryl, having from one to 10 carbon atoms, and $R^3$ can be selected from among H, $C_1$-$C_8$ alkyl, $C_1$-$C_8$ alkoxy, $C_3$-$C_{10}$ cycloaliphatic and $C_6$-$C_{12}$ aryl.

In one embodiment, the number of ligands of the formula (I) is equal to the valence of the metal M.

In further embodiments, $G_1$ in the complex is selected from among $C_1$-$C_{12}$ alkyl (wherein said alkyl is devoid of any pendant amine functionality), alkoxyalkyloxyalkyl, hydrazidyl, aminoalkylaminoalkyl, alkoxyphenyl, alkoxyphenylalkyl, aminoalkyl, and aminophenyl, wherein: the alkyl and alkoxy groups contain 1-3 carbon atoms; amino is —$NH_2$ or monoalkylamino wherein the alkyl on the amino contains 1-3 carbon atoms; and wherein the alkoxyphenyl may optionally be additionally substituted on the phenyl ring by up to two alkyl and/or alkoxy groups, each containing 1-3 carbon atoms.

In another embodiment of the invention, the $G_1$, $R^1$, $R^2$ and $R^3$ substituents are selected such that the precursor is volatilizable at temperature below 300° C. For vapor deposition applications such as chemical vapor deposition and atomic layer deposition, the precursor desirably exhibits good transport properties, without undue susceptibility to degradation and decomposition reactions, and effectively deposits the metal of the central atom on the substrate under conditions of the vapor deposition process that is employed.

In one embodiment, the invention relates to strontium and barium precursors having beta-ketoiminato ligands of the formula (I) above, and their use in vapor deposition processes such as atomic layer deposition.

Such strontium and barium precursors utilize sterically demanding beta-ketoiminato ligands in homoleptic and monomeric complexes that are useful as ALD precursors. The sterically demanding ligands impart to the strontium and barium precursors an extremely low susceptibility to oligomerization, and superior volatilization, transport, stability and deposition properties at temperatures compatible with ALD and CVD processes.

In contrast to traditionally employed strontium and barium complexes used in ALD processes, which exhibit disadvantages including high (>300° C.) transport temperatures and non-conformal surface coverage, the monomeric barium and strontium complexes of the present invention enable low (<300° C.) transport temperatures to be used, and by limiting oligomerization behavior achieved highly conformal films to be formed on the substrate.

The precursors of the invention can be delivered by various delivery techniques, including liquid delivery in which the precursor complex is dissolved in a suitable solvent medium, then volatilized to form a precursor vapor that is transported to the deposition chamber for contacting with the substrate on which the metal-containing film is to be formed, or solid delivery, in which the solid precursor complex is heated to form the precursor vapor for flow to the deposition chamber and contacting with the substrate.

The ketoiminate strontium and barium precursors of the invention in one embodiment include a central atom to which is coordinated multiple ketoiminate ligands. The ketoiminate ligands are coordinated at their nitrogen and oxygen atoms to the central strontium or barium atom, with the nitrogen having a pendant side arm substituent thereon including a neutral donor group capable of interacting with the strontium or barium central atom, and the α-carbons each being substituted with an organo, e.g., a hydrocarbyl, substituent.

The pendant side arm substituent in one embodiment of the invention is selected from the group consisting of alkoxyalkyloxyalkyl, hydrazidyl, aminoalkylaminoalkyl, alkoxyphenyl, alkoxyphenylalkyl, aminoalkyl, and aminophenyl, wherein: the alkyl and alkoxy groups contain 1-3 carbon atoms; amino is —$NH_2$ or monoalkylamino wherein the alkyl on the amino contains 1-3 carbon atoms; and wherein the alkoxyphenyl may optionally be additionally substituted on the phenyl ring by up to two alkyl and/or alkoxy groups, each containing 1-3 carbon atoms.

The ogano substituents on the α-carbons of the ketoiminate ligand may be straight or branched chain alkyl containing 1-6 carbon atoms, and preferably are branched alkyl, e.g., tertbutyl substituents.

An illustrative metal ketoiminate according to one embodiment of the invention, having having α-carbon t-butyl groups, wherein n is the valence of the central metal atom is set out below.

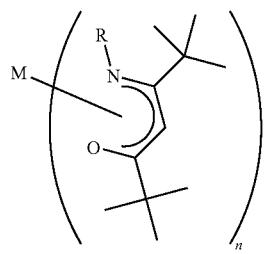

In this ketoiminate, R can be any functional group including pendant side arm functionalities that provide electron donor character. Illustrative examples include alkoxyalkyloxyalkyl, hydrazidyl, aminoalkylaminoalkyl, alkoxyphenyl, alkoxyphenylalkyl, aminoalkyl, and aminophenyl substituents, wherein: the alkyl and alkoxy groups contain 1-3 carbon atoms; amino is —$NH_2$ or monoalkylamino wherein the alkyl on the amino contains 1-3 carbon atoms; and wherein the alkoxyphenyl may optionally be additionally substituted on the phenyl ring by up to two alkyl and/or alkoxy groups, each containing 1-3 carbon atoms.

The metal M can be of any suitable type and can for example be selected from among Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr and Ru.

A representative synthetic scheme for an illustrative Sr or Ba ketoiminate having α-carbon t-butyl groups and a stabilization arm on the ketoiminate nitrogen atom is shown below,

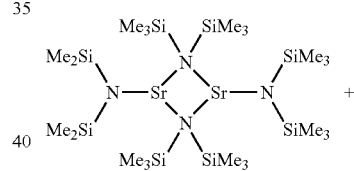

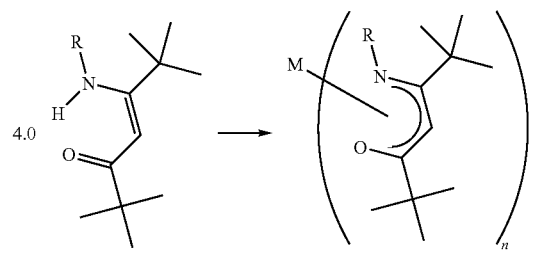

where R can be any electron donor side arm stabilization group that increases the coordination of the associated ligand to the strontium central metal atom, and n is 2 or 3.

The use of pendant side arm functionalities in the ketoiminate ligand facilitates monomeric structure and enhances stability, as shown below, wherein the N atoms in the nitrogen donor side arms coordinate with the central metal atom in a stable complex.

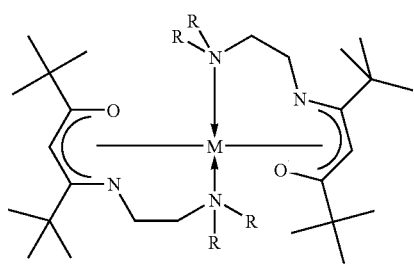

One exemplary form of the stabilized metal ketoiminate complex of the invention is shown below

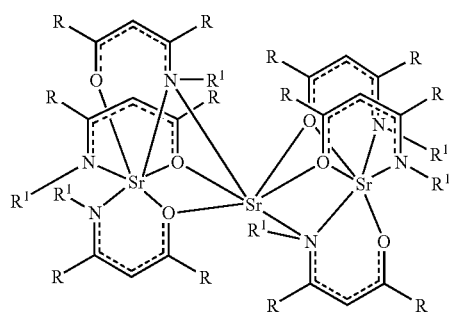

wherein each of the α-carbon R groups is independently selected from among alkyl, fluoroalkyl, clycloaliphatic and aryl, having from one to 10 carbon atoms, and each of the R¹ stabilization donor side arm groups is independently selected from among alkoxyalkyloxyalkyl, hydrazidyl, aminoalkylaminoalkyl, alkoxyphenyl, alkoxyphenylalkyl, aminoalkyl, and aminophenyl, wherein: the alkyl and alkoxy groups contain 1-3 carbon atoms; amino is —NH$_2$ or monoalkylamino wherein the alkyl on the amino contains 1-3 carbon atoms; and wherein the alkoxyphenyl may optionally be additionally substituted on the phenyl ring by up to two alkyl and/or alkoxy groups, each containing 1-3 carbon atoms.

A strontium ketoiminate of such formula, having α-carbon t-butyl groups as the R substituents, and R¹ diethylaminoethyl groups, has the STA plot shown in FIG. 1, and exhibits a melting point of 113° C., a t50 of 276° C., and a residual mass of 15%.

Additional donor arm structures are shown below for ketoiminate ligands that are coordinatable with various metal central atoms, e.g., Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr or Ru.

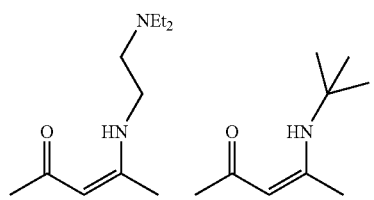

-continued

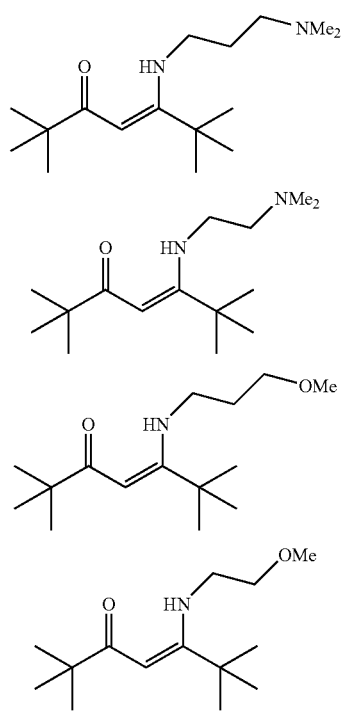

strontium complexes, the donor arm moiety may be any of the species set out in the following formulae:

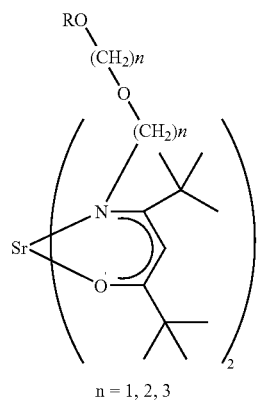

n = 1, 2, 3

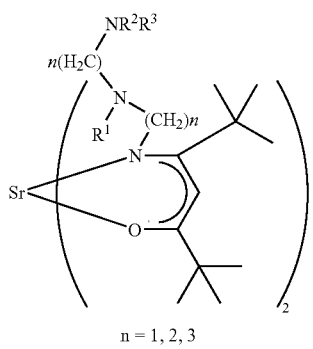

n = 1, 2, 3

-continued

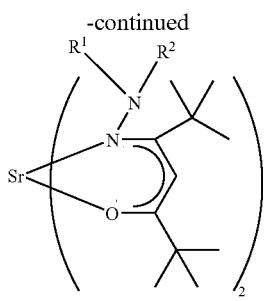

In the foregoing formulae, R, $R^1$, $R^2$, and $R^3$, as applicable, in specific embodiments are independently selected from among H, $C_1$-$C_8$ alkyl, $C_1$-$C_8$ alkoxy, $C_3$-$C_{10}$ cycloaliphatic and $C_6$-$C_{12}$ aryl.

In another aspect, the invention contemplates beta-enaminoesters and their corresponding beta-iminoestrates as CVD/ALD precursors. These precursors encompass beta-enaminoester and beta-iminoestrate ligands coordinated to a metal central atom, e.g., main group metal elements, lanthanides, and transition metals, in complexes of varied types for use in the growth of oxide films for manufacture of microelectronic devices, e.g., dynamic random access memory (DRAM) and gate dielectric structures.

Beta-enaminoesters, as starting materials for making beta-iminoesterates, can be obtained by condensation of amines with beta-ketoesters, with the various substituents $OR^1$, $R^2$, $R^3$ and $R^4$ being readily varied in the synthesis of such precursors, to form a corresponding variety of precursors having utility for vapor deposition applications. The beta-enaninoester ligand compound is shown below, followed by the coordinated ligand in the metal complex:

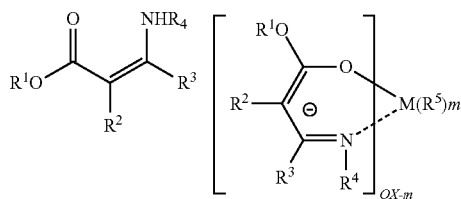

wherein each of $R^1$, $R^2$, $R^3$, $R^4$ and $R^5$ is independently selected from among H, $C_1$-$C_8$ alkyl, $C_1$-$C_8$ alkoxy, $C_3$-$C_{10}$ cycloaliphatic and $C_6$-$C_{12}$ aryl, OX is the oxidation state of the metal M, and m is an integer having a value of from 0 to OX, and $R^1O$ can additionally be cycloalkoxy.

The beta-iminoesterates of the invention have the formula: $[(R^1O)C(\!\!=\!\!O)C(R^2)CR^3(NR^4)]_{OX-m}M(R^5)_m$, wherein each of $R^1$, $R^2$, $R^3$, $R^4$ and $R^5$ is independently selected from among H, $C_1$-$C_8$ alkyl, $C_1$-$C_8$ alkoxy, $C_3$-$C_{10}$ cycloaliphatic and $C_6$-$C_{12}$ aryl, OX is the oxidation state of the metal M, and m is an integer having a value of from 0 to OX, $R^1O$ can additionally be cycloalkoxy and $R^5$ can additionally be selected from amininates, guanidinates, and isourates.

The metals in the foregoing precursors can be any metal with which the ligands are compatible. Illustrative metals include, without limitation, Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr and Ru.

The invention relates in a further aspect to metal ketoesters and malonates as precursors for CVD/ALD applications.

Although beta-diketonates have been widely employed as CVD precursors for corresponding metal, metal oxide and nitride films, for applications involving higher process temperatures, such as high k metal oxide films in DRAM applications, more thermally stable precursors are desirable. By changing substitutions on the chelate ring of the diketonate from alkyl to alkoxy, stronger electron donation capability is achievable for stabilization of electrophilic metal centers, e.g., Ti(+4), Zr(+4), Hf (+4), Sr (+), Ba(2+), Ln(+3), Ta (+5), etc.

The invention therefore contemplates in another aspect precursors selected from among:

ketoesters of the formula $(R)_nM[(R^1O)C(\!\!=\!\!O)C(R^2)C(O)(R^3)]_{OX-n}$, wherein each of R, $R^1$, $R^2$ and $R^3$ is independently selected from among H, $C_1$-$C_8$ alkyl, $C_1$-$C_8$ alkoxy, $C_3$-$C_{10}$ cycloaliphatic and $C_6$-$C_{12}$ aryl, and R can additionally be $-O(CR^4R)_mO-$, wherein each of $R^4$ and $R^5$ is independently selected from among H, $C_1$-$C_8$ alkyl, $C_1$-$C_8$ alkoxy, $C_3$-$C_{10}$ cycloaliphatic and $C_6$-$C_{12}$ aryl and m is an integer having a value of from 1 to 3, OX is the oxidation state of the metal M, and m is an integer having a value of from 0 to OX; and malonates of the formula $(R)_nM[(R^1O)C(\!\!=\!\!O)C(R^2)C(O)(OR^3)]_{OX-n}$, wherein each of R, $R^1$, $R^2$ and $R^3$ is independently selected from among H, $C_1$-$C_8$ alkyl, $C_1$-$C_8$ alkoxy, $C_3$-$C_{10}$ cycloaliphatic and $C_6$-$C_{12}$ aryl, and R can additionally be $-O(CR^4R^5)_mO-$, wherein each of $R^4$ and $R^5$ is independently selected from among H, $C_1$-$C_8$ alkyl, $C_1$-$C_8$ alkoxy, $C_3$-$C_{10}$ cycloaliphatic and $C_6$-$C_{12}$ aryl and m is an integer having a value of from 1 to 3, OX is the oxidation state of the metal M, and n is an integer having a value of from 0 to OX.

These ketoesters and malonates have the formulae:

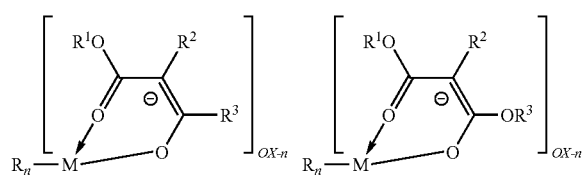

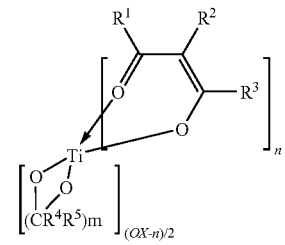

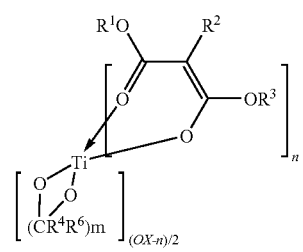

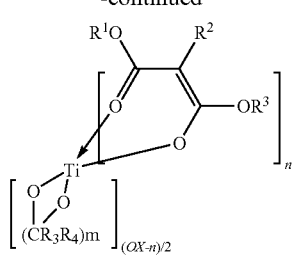

The metal in these ketoester and malonate precursors is any suitable metal with which the ligands are compatible. Illustrative metals include, without limitation, Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr and Ru.

Such precursors can be used for forming metal, metal oxide, metal nitride and any other combinations of such films, utilizing suitable CVD/ALD processes, and appropriate delivery systems and co-reactants.

A further aspect of the invention relates to titanium precursors useful in forming Ti-containing films, such as SrTiO films. The titanium precursors have the formula:

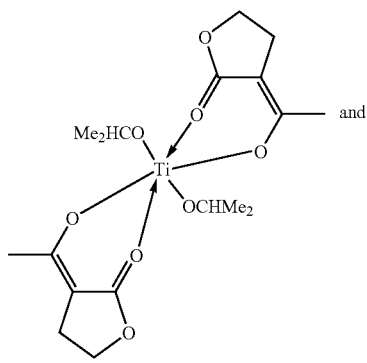

such as may be formed by the following synthesis reactions:

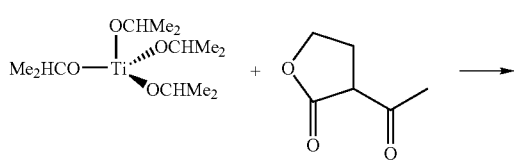

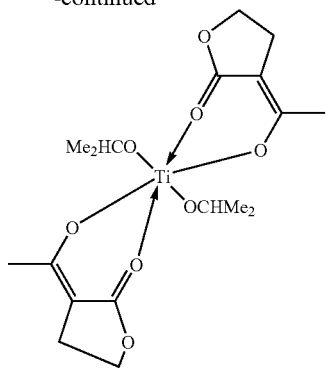

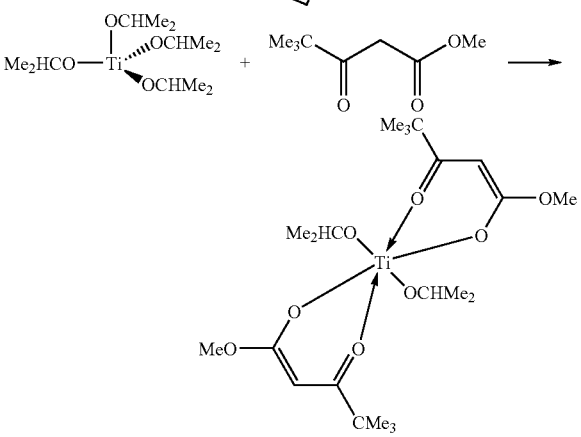

respectively.

Such titanium precursors can be utilized for liquid delivery to deposit Ti on a substrate, e.g., in a solvent such as pentane or other aliphatic hydrocarbon solvent.

As an illustrative example demonstrating the use of the precursor metal complexes of the invention for forming a metal-containing film on a substrate, a strontium precursor complex in accordance with the invention is dissolved in an organic solvent, such as tetrahydrofuran (THF), toluene, o-xylene, or other suitable solvent, to form a corresponding precursor solution for liquid delivery. The concentration of the precursor in the solution can be for example in a range of from 0.01M to 0.5 M, e.g., 0.10 M. The solution is delivered to a vaporizer and heated to temperature in a range of from 100 to 200° C., to vaporize the precursor solution and form a precursor vapor. The precursor vapor is pulsed into an atomic layer deposition (ALD) reactor for a period of time that may range from 0.1 second to 60 seconds depending on the specific application, for contact with the substrate to deposit the metal-containing film thereon. The reactor then is purged with inert gas (e.g., Ar or He) for a period of time that may be in a range of from 1 to 60 seconds, following which $O_3$ is flowed into the reactor, and an SrO layer is formed on the substrate. Following this deposition of strontium oxide on the substrate, a $TiO_2$ layer is grown on the SrO layer on the substrate. The foregoing sequence of deposition steps then is successively repeated, until a desired film thickness (e.g., ~10 to 20 nm thickness) of a strontium titanate (STO) thin film is produced.

Figure 2:
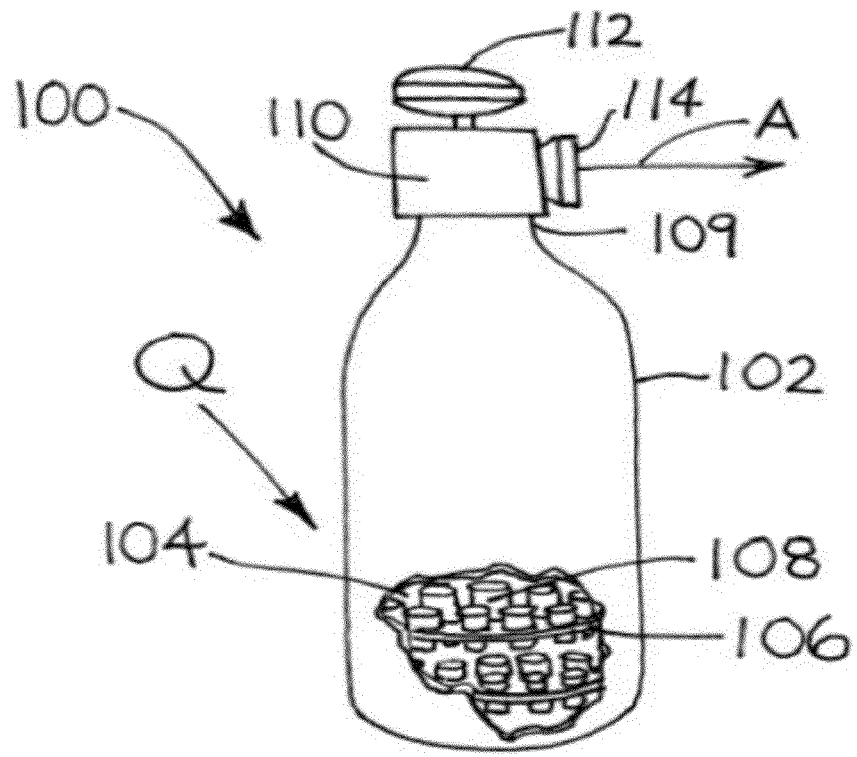
FIG. 2 is a schematic representation of a material storage and dispensing package containing a precursor of the present invention, in one embodiment thereof.

FIG. 2 is a schematic representation of a material storage and dispensing package 100 containing a barium or strontium precursor, according to one embodiment of the present invention.

The material storage and dispensing package 100 includes a vessel 102 that may for example be of generally cylindrical shape as illustrated, defining an interior volume 104 therein. In this specific embodiment, the precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly, for dispensing in use of the vessel.

The solid precursor can be coated on interior surfaces in the interior volume of the vessel, e.g., on the surfaces of the trays 106 and conduits 108. Such coating may be effected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein.

The vessel 102 has a neck portion 109 to which is joined the valve head assembly 110. The valve head assembly is equipped with a hand wheel 112 in the embodiment shown. The valve head assembly 110 includes a dispensing port 114, which may be configured for coupling to a fitting or connection element to join flow circuitry to the vessel. Such flow circuitry is schematically represented by arrow A in FIG. 1, and the flow circuitry may be coupled to a downstream ALD or chemical vapor deposition chamber (not shown in FIG. 2).

In use, the vessel 102 is heated, such input of heat being schematically shown by the reference arrow Q, so that solid precursor in the vessel is at least partially volatilized to provide precursor vapor. The precursor vapor is discharged from the vessel through the valve passages in the valve head assembly 110 when the hand wheel 112 is translated to an open valve position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal on the substrate as a film thereon.

In one embodiment, the precursor is dissolved in an ionic liquid medium, from which precursor vapor is withdrawn from the ionic liquid solution under dispensing conditions.

As a still further alternative, the precursor may be stored in an adsorbed state on a suitable solid-phase physical adsorbent storage medium in the interior volume of the vessel. In use, the precursor vapor is dispensed from the vessel under dispensing conditions involving desorption of the adsorbed precursor from the solid-phase physical adsorbent storage medium.

Supply vessels for precursor delivery may be of widely varying type, and may employ vessels such as those commercially available from ATMI, Inc. (Danbury, Conn.) under the trademarks SDS, SAGE, VAC, VACSorb, and ProE-Vap, as may be appropriate in a given storage and dispensing application for a particular precursor of the invention.

The precursors of the invention thus may be employed to form precursor vapor for contacting with a substrate to deposit a metal-containing film, e.g., a barium- and/or strontium-containing thin film thereon.

Precursors of the invention can be used in single precursor formulations or alternatively in multi-precursor formulations, as is desirable in a given end use application of the invention.

In a preferred aspect, the invention utilizes the precursor(s) to conduct atomic layer deposition, yielding ALD films of superior conformality that are uniformly coated on the substrate with high step coverage and conformality even on high aspect ratio structures.

Accordingly, the precursors of the present invention enable a wide variety of microelectronic devices, e.g., semiconductor products, flat panel displays, etc., to be fabricated with metal-containing films of superior quality.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A precursor including a central metal atom M to which is coordinated at least one ligand of formula (I):

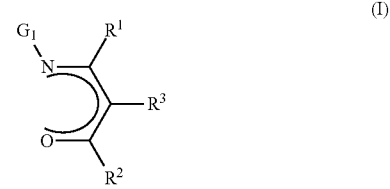

wherein:
$R^1$, $R^2$ and $R^3$ are each independently H or ogano moieties; and
$G_1$ is an electron donor arm substituent that increases the coordination of the ligand to the central metal atom M;
wherein when $G_1$ is aminoalkyl, the substituents on the amino nitrogen are not alkyl, fluoroalkyl, cycloaliphatic, or aryl, and are not connected to form a ring structure containing carbon, oxygen or nitrogen atoms, and wherein the metal M is selected from the group consisting of Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, Mn, Co, Ni, Zn, Cd, Te, Hg, Au, Cu, Ag, Sr and Ru.

2. The precursor of claim 1, wherein each of $R^1$ and $R^2$ is the same as or different from one another, with each being independently selected from among alkyl, fluoroalkyl, cycloaliphatic and aryl, having from one to 10 carbon atoms, and $R^3$ is selected from among H, $C_1$-$C_8$ alkyl, $C_1$-$C_8$ alkoxy, $C_3$-$C_{10}$ cycloaliphatic and $C_6$-$C_{12}$ aryl.

3. The precursor of claim 1, wherein the number of ligands of the formula (I) is equal to the valence of the metal M.

4. The precursor of claim 1, wherein $G_1$ in the complex is selected from among $C_1$-$C_{12}$ alkyl, alkoxyalkyloxyalkyl, hydrazidyl, aminoalkylaminoalkyl, alkoxyphenyl, alkoxyphenylalkyl, aminoalkyl, and aminophenyl, wherein: the alkyl and alkoxy groups contain 1-3 carbon atoms; amino is —$NH_2$ or monoalkylamino wherein the alkyl on the amino contains 1-3 carbon atoms; and wherein the alkoxyphenyl may optionally be additionally substituted on the phenyl ring by up to two alkyl and/or alkoxy groups, each containing 1-3 carbon atoms.

5. The precursor of claim 1, wherein the $G_1$, $R^1$, $R^2$ and $R^3$ substituents are selected such that the precursor is volatilizable at temperature below 300° C.

6. The precursor of claim 1, wherein M is selected from among strontium and barium.

7. A precursor of the formula

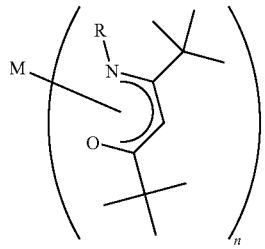

wherein R is a functional group including pendant side arm functionality that provides electron donor character, n is the valence of the metal M, and M is selected from the group consisting of Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr and Ru.

8. The precursor of claim 7, wherein R is selected from among alkoxyalkyloxyalkyl, hydrazidyl, aminoalkylaminoalkyl, alkoxyphenyl, alkoxyphenylalkyl, aminoalkyl, and aminophenyl substituents, wherein: the alkyl and alkoxy groups contain 1-3 carbon atoms; amino is —$NH_2$ or monoalkylamino wherein the alkyl on the amino contains 1-3 carbon atoms; and wherein the alkoxyphenyl may optionally be additionally substituted on the phenyl ring by up to two alkyl and/or alkoxy groups, each containing 1-3 carbon atoms.

9. A precursor including a metal M to which is coordinated a ligand selected from among

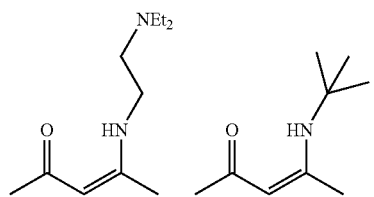

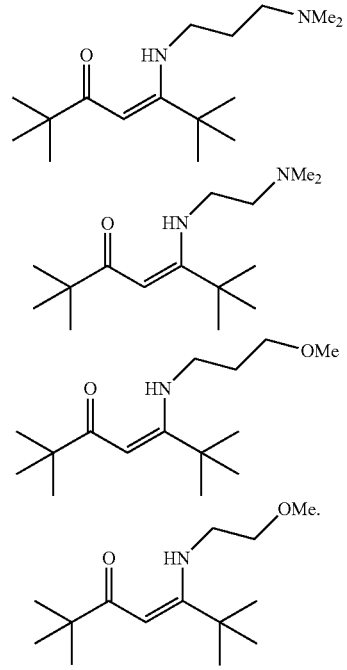

10. The precursor of claim 9, wherein the metal M is selected from among Ta, V, Ti, Nb, Pb, Ni, W, Ca, Ba, In, Y, La, Zr, Hf, Ir, Ru, Pt, Pd, Os, Re, Cr, Mo, Ge; Al, Si, Ga, Sc, V, Cr, Fe, Sb, Bi, lanthanides, Mn, Co, Ni, Zn, Cd, Te, Hg, Au, Cu, Ag, Sr and Ru.

11. A precursor composition comprising a precursor according to claim 1, in a solvent medium.

12. A precursor composition comprising a precursor according to claim 7, in a solvent medium.

13. A precursor composition comprising a precursor according to claim 9, in a solvent medium.

14. The precursor composition of claim 11, wherein the solvent medium comprises a solvent selected from among tetrahydrofuran (THF), toluene, and o-xylene.

15. The precursor composition of claim 12, wherein the solvent medium comprises a solvent selected from among tetrahydrofuran (THF), toluene, and o-xylene.

16. The precursor composition of claim 13, wherein the solvent medium comprises a solvent selected from among tetrahydrofuran (THF), toluene, and o-xylene.

17. A precursor source package comprising a precursor storage and dispensing vessel holding a precursor according to claim 1.

18. A precursor source package comprising a precursor storage and dispensing vessel holding a precursor according to claim 7.

19. A precursor source package comprising a precursor storage and dispensing vessel holding a precursor according to claim 9.

* * * * *

UNITED STATES PATENT AND TRADEMARK OFFICE
CERTIFICATE OF CORRECTION

PATENT NO. : 8,168,811 B2
APPLICATION NO. : 12/507048
DATED : May 1, 2012
INVENTOR(S) : Thomas M. Cameron It is certified that error appears in the above-identified patent and that said Letters Patent is hereby corrected as shown below:

Column 10, lines 35-42:

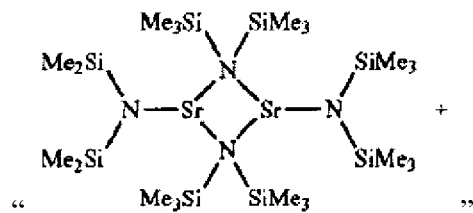

should be

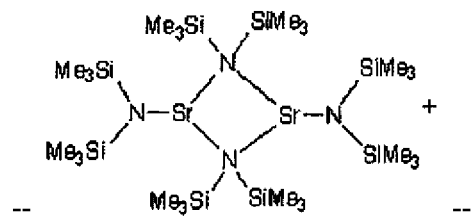

Signed and Sealed this
Thirteenth Day of November, 2012

David J. Kappos
*Director of the United States Patent and Trademark Office*